(12) United States Patent
Dakka et al.

(10) Patent No.: US 6,914,166 B2
(45) Date of Patent: Jul. 5, 2005

(54) PROCESS FOR THE SELECTIVE DIMERIZATION OF ISOBUTENE

(75) Inventors: Jihad Mohammed Dakka, White House Station, NJ (US); Marc O. J. Geelen, Halle (BE); Georges Marie Mathys, Bierbeek (BE); Paul William Allen, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 402 days.

(21) Appl. No.: 10/130,146

(22) PCT Filed: Dec. 20, 2000

(86) PCT No.: PCT/US00/34840

§ 371 (c)(1),
(2), (4) Date: Aug. 13, 2002

(87) PCT Pub. No.: WO01/46095

PCT Pub. Date: Jun. 28, 2001

(65) Prior Publication Data

US 2003/0100811 A1 May 29, 2003

(51) Int. Cl.$^7$ .................................................. C07C 2/12
(52) U.S. Cl. ....................................... 585/533; 585/512
(58) Field of Search .................................. 585/533, 512

(56) References Cited

U.S. PATENT DOCUMENTS

| | | | |
|---|---|---|---|
| 2,276,199 A | 3/1942 | Kassel | 196/10 |
| 3,325,465 A | 6/1967 | Jones et al. | 260/94.9 |
| 4,454,367 A | 6/1984 | Sakurada et al. | 585/533 |
| 5,065,794 A | 11/1991 | Cheung | 137/883 |
| 5,091,590 A | 2/1992 | Harandi et al. | 568/697 |
| 5,401,429 A | 3/1995 | Flynn et al. | 252/171 |
| 5,910,528 A | 6/1999 | Falicoff et al. | 524/315 |

FOREIGN PATENT DOCUMENTS

| | | |
|---|---|---|
| DE | 35 42171 A1 | 6/1985 |
| EP | 0736584 B1 | 10/1998 |
| EP | 0 994 088 | 4/2000 |
| WO | WO 91 18851 | 12/1991 |

*Primary Examiner*—Thuan D Dang

(57) ABSTRACT

The present invention relates to processes for making a reaction product comprising trimethylpentene(s) which comprises contacting a $C_4$ olefinic feedstock containing isobutene and n-butene(s) with a catalyst comprising zeolite beta under conditions allowing selective dimerization of isobutene to trimethylpentene(s). It also relates to the products obtained by these processes.

8 Claims, No Drawings

PROCESS FOR THE SELECTIVE DIMERIZATION OF ISOBUTENE

The present invention relates to selective processes for making a reaction product comprising trimethylpentene(s) from a C4 olefinic feedstock. It also relates to products obtained by such processes.

Isobutene oligomers are useful intermediates for the preparation of various products of commercial interest, such as isoparaffins, higher alcohols, aldehydes or carboxylic acids having 8, 12 or 16 carbon atoms. Amongst such products, highly branched trimethylpentanes that can be obtained through hydrogenation of trimethylpentenes are of particular interest as gasoline octane number enhancers. Indeed, trimethylpentanes have high RONs (Research Octane Numbers) and MONs (Motor Octane Numbers): 2,2,4-trimethylpentane, also known as isooctane, has a RON of 100 and a MON of 100; 2,3,4-trimethylpentane has a RON of 109.27 and a MON of 95.9; 2,2,3-trimethylpentane has a RON of 109.9 and a MON of 99.9.

One route to produce trimethylpentenes is to dimerise isobutene. However, efficient production of trimethylpentenes from isobutene requires that the process be selective for dimers over oligomers. Oligomerization of isobutene may occur under various acidic conditions using phosphoric acid, trifluoroboron, alumino-silicate or zeolite-containing catalysts. However, such processes usually give mixtures of dimers, trimers, tetramers and higher molecular weight oligomers.

Selective dimerisation of isobutene over trimerisation and higher oligomerisation is known from U.S. Pat. No. 3,325,465 and DE 3,542,171-A1.

In U.S. Pat. No. 3,325,465, olefinic hydrocarbons having two to six carbon atoms are dimerised to the substantial exclusion of trimers and higher polymers by conducting the polymerisation over aluminosilicates which have been exchanged with nickel or cobalt ions. Dimerization of isobutene is shown to occur over a 13× molecular sieve which has 95.9 percent of its sodium ions exchanged by cobalt ions with a rate of conversion into dimer over 90 percent, even approaching 100 percent. However, the exact composition of the dimer product is not given. DE 3,542,171-A1 discloses selective dimerisation of isobutene into 2,4,4-trimethylpent-1-ene and -2-ene, using a bismuth and/or lead doped zeolite catalyst at 150° C. Selectivity for dimer over trimer formation can be as high as 88 percent.

The processes disclosed in U.S. Pat. No. 3,325,465 and in DE 3,542,171-A1 are thus selective means for obtaining isobutene dimers from an isobutene feedstock. However, on an industrial scale, it would be more advantageous to use industrial C4 olefinic feedstocks as obtained from petroleum cracking. Such feedstocks are produced in oil refineries, and usually comprise isobutene, 1-butene and 2-butene; they may also comprise butadiene.

A problem associated with the use of isobutene admixed with other C4 olefins is that isobutene oligomerisation conditions produce codimers of isobutene with the other normal C4 olefins of the feedstock in addition to the desired isobutene homodimers, i.e., trimethylpentenes. Selective production of trimethylpentenes from a mixed C4 olefinic feedstock thus requires highly selective process conditions. Catalysts used in such process must not only be selective for dimers over higher oligomers, but they must also favor isobutene homodimerisation over codimerisation of isobutene with the other normal C4 olefins of the feedstock.

Oligomerisation of isobutene from a mixture of C4 olefins over zeolite catalysts has been disclosed in U.S. Pat. No. 4,454,367 and U.S. Pat. No. 5,091,590.

U.S. Pat. No. 4,454,367 discloses a method for converting isobutene into low polymers, i.e., a mixture of isobutene dimers, trimers and tetramers, from a C4 olefinic mixture comprising isobutene and n-butenes. The process uses as catalyst a high silica mordenite having a SiO2/Al2O3 mole ratio of 50 to 200 and advantageously forms low polymers of isobutene. In the examples, a C4 hydrocarbon mixture consisting of 26.2 mole % of butane, 1.3 mole % of isobutene, 7.5 mole % of 1-butene and 65 mole % of 2-butene was fed into a reactor packed with the high silica mordenite at a temperature of 80° C. Under these conditions isobutene conversion rates of up to 93 percent were achieved with low n-butene loss.

U.S. Pat. No. 5,091,590 discloses a two-stage method for MTBE (methyl tertiary butyl ether) preparation from a C4 feedstock comprising isobutene, 1-butene and/or 2-butene. In the first stage of the process, the C4 feedstock is treated with methanol over solid acid etherification catalyst particles (first reaction zone). This produces an intermediate product containing MTBE and unreacted feedstock, including 10–55% unreacted isobutene from the fresh feedstock and excess methanol. The intermediate product is withdrawn from the first reaction zone and fractionated to recover MTBE. The remaining part of the intermediate product then undergoes the second stage of the process; it is contacted with medium pore solid acid catalyst particles to give a product containing MTBE, isobutene oligomer and C5+ alkylate. The preferred catalyst for this second stage is selected from ZSM-5, ZSM-11, ZSM-50, zeolite beta, MCM-22 and mixtures thereof. According to this document, the second stage reaction takes place at 70° to 280° C.

We have now found other process conditions for removing isobutene from industrial C4 olefinic feedstocks that are selective for trimethylpentenes over other C8 olefins and higher oligomers.

Accordingly, the present invention provides a process for making a reaction product comprising trimethylpentene(s) which comprises contacting a C4 olefinic feedstock containing isobutene and n-butene(s) with a catalyst comprising zeolite beta under conditions allowing selective dimerization of isobutene to trimethylpentene(s).

In addition to isobutene, the C4 olefinic feedstock used in the present process may comprise n-butene, i.e., 1-butene and/or 2-butene. Optionally, these feedstocks may also contain butadiene. Suitable C4 olefinic feeds include C4 hydrocarbon mixtures obtained in refining, cracking (catalytic cracking or steam cracking) and/or reforming of oils, butane-butene fractions obtained by removing butadiene from C4 by-product fractions formed in the production of ethylene by thermal cracking of oils or C4 hydrocarbon mixtures obtained by dehydrogenation of hydrocarbon mixtures containing n-butane and isobutane.

The present process advantageously oligomerizes isobutene without the need for prior separation of isobutene from the feed. Another advantage of the present process is that it is highly selective for isobutene homooligomerization versus isobutene/n-butene codimerization. Less than 10 wt %, preferably less than 5 wt % of the n-butenes present in the feedstock are oligomerised. Such selectivity is achieved with a catalyst comprising zeolite beta.

For the purposes of the present process, zeolite beta is in proton form, herewith referred to as zeolite H-beta. Zeolite H-beta is a zeolite with relatively large pores. It is available commercially or may be prepared synthetically in different Si/Al atomic ratios ranging for example from 10 to 150. Reference is made to "Synthesis of High Silica Aluminosilicate Zeolites" by P. A. Jacobs and J. A. Martens (published as volume 33 in the series "Studies in Surface Science and Catalysis") for a review of the synthesis and properties of zeolite beta. Zeolite beta with Si/Al atomic ratios higher than 150 can be obtained by dealumination methods such as hydrothermal (steaming) and/or chemical treatment. We refer to "Introduction to Zeolite Science and Practice", H. Van Bekkum et al., Elsevier 1991, for further details on dealumination. Such dealuminated zeolite H-beta may also be used in the present process.

The zeolite beta catalyst may be used in the form of powders (including powders consisting wholly or in part of single crystals). The zeolite beta catalyst may instead be incorporated in shaped agglomerates, for example, tablets, extrudates or spheres, which may be obtained by combining the zeolite with a binder material that is substantially inert under the conditions employed in the oligomerization process. The zeolite catalyst may be present in amounts from 1 to 99% by weight, based on the combined weight of the zeolite and binder material. As binder material there may be used any suitable material, for example silica, metal oxides, or clays, such as montmorillonite, bentonite and kaolin clays, the clays optionally being calcined or modified chemically prior to use. Further examples of such suitable matrix materials include silica-alumina, silica-berylia, silica-magnesia, silica-thoria, silica-titania, silica-alumina-magnesia, silica-alumina-thoria, silica-alumina-zirconia and silica-magnesia-zirconia.

The process according to the present invention may be carried out in various types of reactors suited for heterogenous reactions, either fixed or fluid bed reactors. The process may be carried out in batch or continuous flow reactors or according to the catalytic distillation technique (also called reactive distillation). Conversion of isobutene from the C4 olefinic feedstock can take place under liquid, vapor or mixed phases.

The present process selectively converts isobutene present in the C4 olefinic feedstock into a reaction product comprising trimethylpentenes: dimers represent at least 45 wt %, preferably 60 wt % of all oligomers formed, and trimethylpentenes represent at least 80 wt % of all dimers formed. Such selectivities for trimethylpentenes may be achieved at moderate temperatures, e.g., below 50° C.

Accordingly, the present invention also encompasses the products obtained by contacting a C4 olefinic feedstock with a catalyst comprising zeolite beta. Said products may be transformed into other products of commercial interest by one or several conversion steps, e.g., fractionation, hydrogenation, hydroformylation followed by oxidation or hydrogenation, carbonylation, etherification, epoxidation or hydration. The present invention also encompasses the products obtained by these further transformation, e.g., alkanes, alcohols, ethers, aldehydes, epoxides or carboxylic acids.

In a specific example, dimerisation of isobutene from the C4 olefinic feedstock may be carried out in the presence of an alcohol. In such a case, etherification of trimethypentenes takes place at the same time as dimerization of isobutene.

The following non-limiting examples illustrate the present invention.

Selective dimerisation of isobutene from an industrial C4 olefinic feedstock in the presence of various zeolite H-beta catalysts was studied as follows.

The zeolite catalyst (10 wt % of the olefinic feedstock) and C4 olefinic feedstock (having the following composition, expressed in wt %: 12% isobutane, 19% n-butane, 14% 1-butene, 20.2% isobutene, 20.5% trans-2-butene and 13.1% cis-2-butene) were loaded into a 1 liter reactor equipped with a heating element and mechanical stirring. The reactor was pressurized with argon up to 10 bars. The mixture was then heated to 40° C. and kept at that temperature for 2 hours. After reaction, the reactor was cooled down and sampled under pressure.

The composition of product mixture was then determined by gas chromatography (GC), using hydrogen as carrier gas. The injector liner was filled with a hydrogenation catalyst (0.03 g of 0.5% Pt on Al) so that, by in-situ hydrogenation, all the components were identified as paraffins. The conversion of butenes/isobutene was determined by comparing the GC analysis of the product mixture with the GC analysis of the feedstock under the same conditions. The feedstock contains butane and isobutane which are inert under the reaction conditions; butane and isobutane were thus used as internal standards for calculating conversion.

The catalysts tested were:

H-Beta 10: zeolite H-beta having Si/Al atomic ratio of 10.5, commercially available from Zeolyst International;

H-Beta 30: zeolite H-beta having Si/Al atomic ratio of 30, obtained from a zeolite beta in Na form that has been calcined at 550° C. for 16 hours under air and then exchanged with 0.5 N aqueous $NH_4Cl$ (100 ml solution for 1 g catalyst) under reflux for 12 hours, then dried and calcined at 550° C. for 10 hours under air. The zeolite beta in Na form used in this procedure was prepared synthetically according to the procedure disclosed in EP 187522;

H-Beta 30 st.: H-Beta described above which has been steamed at 650° C. for 16 hours;

H-Beta 30 st. reg.: H-Beta 30 st. described above, which has been regenerated after use by drying and calcinating at 550° C. for 10 hours under air;

H-Beta 30 nitric: H-Beta 30 described above, which has been treated with 6N $HNO_3$ under reflux for 2 hours, filtered and washed until washing liquids were acid free, then dried at 75° C. under vacuum overnight;

H-Beta 50: zeolite H-Beta having Si/Al atomic ratio of 50 commercially available from Süd Chemie;

H-Beta 100: zeolite H-Beta having Si/Al atomic ratio of 100 commercially available from Süd Chemie;

H-Beta 150: zeolite H-beta having Si/Al atomic ratio of 150 commercially available from Süd Chemie;

H-Beta 150 st.: H-beta 150 mentioned above which has been steamed at 650° C. for 16 hours;

H-Beta 150 nitric: H-Beta 150 mentioned above which has been treated with 6N $HNO_3$ under reflux for 2 hours, filtered and washed until washing liquids were acid free, then dried at 75° C. under vacuum overnight.

The Table gives the results obtained with each of these zeolites.

In the Table, iC4=means isobutene;

nC4=means n-butene;

C8 represents the wt % of dimers formed;

C12 represents the wt % of trimers formed;

C16 represents the wt % of tetramers formed;

NC8 represents the wt % of dimers obtained in the form of octenes (octane after hydrogenation);

MC7 represents the wt % of dimers obtained in the form of methylheptenes (methylheptanes after hydrogenation);

DMC6 represents the wt % of dimers obtained in the form of dimethylhexenes (dimethylheptanes after hydrogenation);

TMC5 represents the wt % of dimers obtained in the form of trimethylpentenes (trimethylpentanes after hydrogenation);

2,2,4-TMP represents the portion in wt % of TMC5 in the form of 2,2,4-trimethylpentane (after hydrogenation);

2,3,4-TMP represents the portion in wt % of TMC5 obtained in the form of 2,3,4-trimethylpentane (after hydrogenation).

| Catalyst | Wt (g) | Conversion wt % | | Selectivity wt % | | | C8 branchiness (wt %) after hydrogenation | | | | | |
|---|---|---|---|---|---|---|---|---|---|---|---|---|
| | | iC4 = | nC4 = | C8 | C12 | C16 | NC8 | MC7 | DMC6 | TMC5 | 2,2,4 TMP | 2,3,4 TMP* |
| H-Beta 10 | 10.0 | 87 | 4 | 60 | 28 | 10 | 0.0 | 0.0 | 11 | 89 | 45 | 5 |
| H-Beta 30 | 10.2 | 93 | 6 | 60 | 30 | 8 | 0.0 | 0.0 | 16 | 84 | 49 | 7 |
| H-Beta 30 st. | 9.5 | 50 | 0 | 68 | 24 | 6 | 0.0 | 0.0 | 3 | 97 | 90 | 3 |
| H-Beta 30 st. reg. | 7.5 | 56 | 0 | 71 | 27 | 0 | 0.0 | 0.0 | 3 | 97 | 91 | 1 |
| H-Beta 30 nitric | 9.4 | 44 | 0 | 74 | 18 | 5 | 0.0 | 0.0 | 5 | 95 | 82 | 2 |
| H-Beta 50 | 6.4 | 96 | 7 | 58 | 34 | 7 | 0.0 | 0.0 | 16 | 84 | 55 | 77 |
| H-Beta 100 | 8.7 | 100 | 9 | 48 | 33 | 18 | 0.0 | 0.0 | 19 | 81 | 45 | 8 |
| H-Beta 150 | 9.1 | 96 | 6 | 55 | 44 | 0.0 | 0.0 | 0.0 | 15 | 85 | 55 | 6 |
| H-Beta 150 st. | 8.3 | 32 | 0 | 63 | 27 | 7 | 0.0 | 0.0 | 7 | 92 | 79 | 3 |
| H-Beta 150 nitric | 10.0 | 53 | 1 | 63 | 35 | 0.0 | 0.0 | 0.0 | 8 | 92 | 74 | 4 |

Composition feedstock in wt %; 12% iC4 19% nC4 14% nC4 = 1 20.2% iC4 = 20.5% trC4 = 2 13.1% cisC4 = 2
Feedstock is reacted with the catalyst for 2 hrs at 40° C.
*Remainder TMP are 2,2,3 and 3,3,3 trimethyl pentane

We claim:

1. A process for making a reaction product comprising trimethylpentene(s) which comprises contacting a $C_4$ olefinic feedstock containing isobutene and n-butene(s) with a catalyst comprising zeolite beta under conditions allowing selective dimerization of isobutene to trimethylpentene(s), characterized in that said zeolite beta has undergone dealumination prior to use.

2. A process according to claim 1, characterized in that less than 10 wt % of the n-butene(s) present in the $C_4$ olefinic feedstock are oligomerized.

3. A process according to claim 1, characterized in that dealumination of zeolite beta is performed by steaming and/or chemical treatment.

4. A process according to claim 1, characterized in that it is carried out in a batch or continuous flow reactor.

5. A process according to claim 1, characterized in that it is carried out according to the catalytic distillation technique.

6. A process according to claim 1, characterized in that isobutene dimers represent at least 45 wt %, preferably at least 60 wt % of all products formed, and trimethylpentenes represent at least 80 wt % of all dimers formed.

7. A process according to claim 1, characterized in that the reaction temperature is below 50° C.

8. A process according to claim 1, characterized in that it further comprises hydrogenation.

* * * * *